United States Patent [19]

Madsen et al.

[11] 3,941,777

[45] Mar. 2, 1976

[54] COMPOUNDS HAVING JUVENILE HORMONE ACTIVITY

[75] Inventors: Hans Berg Madsen, Bovlingbjerg; Preben Lindholm Holst; Houk Solli, both of Harboor, all of Denmark

[73] Assignee: A/S Cheminova, Lemvig, Denmark

[22] Filed: Dec. 19, 1973

[21] Appl. No.: 426,385

[52] U.S. Cl. ...... 260/240 H; 260/240 R; 260/240 G; 260/296 R; 260/296 M; 260/340.9; 260/348 R; 260/340.5; 260/453 R; 260/500.5 H; 260/514 R; 260/561 R; 260/566 AE; 424/263; 424/282; 424/278; 424/327
[51] Int. Cl.² ............... C07D 303/18; C07C 119/08
[58] Field of Search ....... 260/240 G, 348 R, 296 M, 260/240 R, 240 H, 566 AE, 340.5

[56] References Cited
UNITED STATES PATENTS

| | | |
|---|---|---|
| 2,924,604 | 2/1960 | Steinhards..................... 260/296 M |
| 3,198,803 | 8/1965 | Mathes et al................... 260/296 M |
| 3,205,234 | 7/1965 | Schumann...................... 260/296 M |
| 3,671,558 | 6/1972 | Siddall et al. ................... 260/240 R |
| 3,829,577 | 8/1974 | Chodnekar et al. ............. 260/240.5 |

OTHER PUBLICATIONS

Sadykh-Zade. Chem. Abstracts 71(1969) No. 1127009.
Carter et al. Chem. Abstracts 71 (1969) No. 31439.

*Primary Examiner*—Arthur P. Demers
*Attorney, Agent, or Firm*—Browne, Beveridge, DeGrandi & Kline

[57] ABSTRACT

This invention is concerned with certain alkyl, terpenoid and olefinic oximethers of some aryl, pyridyl and alifatie aldehydes and ketones, and their preparation and use. These compounds possess improved juvenile hormonal activity which can be utilized first and foremost to inhibit the metamosphosis of insert larvae and to act as sterilizing or ovicidal agent, consequently, can be utilized in the control of insects.

6 Claims, No Drawings

COMPOUNDS HAVING JUVENILE HORMONE ACTIVITY

This invention is for improvements in or relating to chemical compounds having juvenile hormone activity. More particularly, the present invention relates to methods and compositions for the control of insects, and to novel alkyl, terpenoid and olefinic oximethers of some aryl, pyridyl and alifatic aldehydes and ketones.

A number of substances are known which have juvenile hormone activity demonstrated by retention of larval and pupal characters, inhibition of metamorphosis and stimulation of ovarian growth in adult females together with ovicidal activity. For a comprehensive review see: Slama, K., Ann. Rev. of Biochem., 40, 1079 (1971).

It is known from the literature that compounds with a terpenoid skeleton attached to various functional groups show juvenile hormone activity. Schwartz, M., et al.: Science, 167, 191–2 (1970) and Journ. Econ. Ent. 63, 1858–60 (1970).

Some compounds of this type exhibit high activity when applied topically to the insect, stimulates its development and prevent formation of sexually mature adults. Compounds exhibitng this activity may be envisaged as potential insecticides of the third generation.

The compounds of the present invention act selectively on certain insects and, moreover, exhibit high sterilizing properties. Compounds, the preparation and application of which is described herein, represent novel analogs of the insect juvenile hormone which are cheaper to prepare and possess higher activity for some insects than many known analogs.

The novel compounds of the present invention are oximethers represented by the following general formula (I)

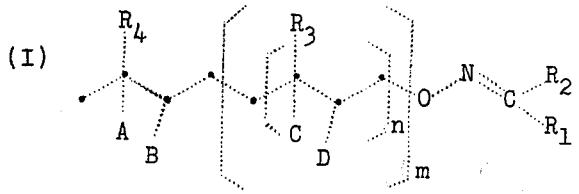

(I)

in which the symbols represents,

- A : hydrogen or an alkyl group or an alkoxy group, preferably with from 1 to 6 carbon atoms,
- B : a hydrogen atom, or,
- A B : when taken together, a further single bond between the adjacent carbon atoms, or an oxygen atom,
- C : a hydrogen atom,
- D : a hydrogen atom, or,
- C D : when taken together, a further single bond between the adjacent carbon atoms,
- $n$ : an integer which is 0 or 1,
- $m$ : an integer which is 0 or 1,
- $R_4$ : a methyl or ethyl group,
- $R_3$ : a methyl or ethyl group,
- $R_1$ : a hydrogen atom, or an alkyl group with from 1 to 6 carbon atoms,
- $R_2$ : an alkyl group, a hydroxy group, an alcohol group (e.g. $-CH_2OH$ or $-C_2H_4OH$), an alkoxy group, an ether residue (e.g., $-CH_2-O-CH_3$), a carboxylic acid group (e.g. $-COOH$ or $-CH_2-COOH$) an ester group (e.g. $-COOR$ or $-CH_2COOR$, where R is an alkyl group), a monodi-, or tri-halogenalkyl group, an amide group, a 3,4-methylenedioxyphenyl group, or the group with the general formula (II)

(II) 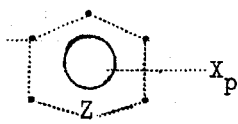

wherein Z in CH or a nitrogen atom, $p$ is an integer from 0 to 3, and X is hydrogen or at least one substituent such as, for example, $NO_2$, halogen, OH, $CF_3$, an alkyl group or an alkoxy group, which substituent X, when $p$ is 2 or 3 may be the same or different.

In all the above definitions, the alkyl, halogenalkyl and alkoxy groups preferably each contain from 1 to 6 carbon atoms. The alkyl is said groups, including the haloalkyl and alkoxy groups, may be straight or branched. As examples may be mentioned methyl, ethyl, propyl, i-propyl, t-butyl, pentyl and hexyl. Preference is given to methyl and ethyl. Preferred compounds of the present invention are compounds of the general formula (I), in which the symbols represents,

- A : hydrogen or an alkyl group or an alkoxy group with 1 or 2 carbon atoms
- B : a hydrogen atom, or,
- A B : when taken together, a further single bond between the adjacent carbon atoms, or an oxygen atom,
- C : a hydrogen atom,
- D : a hydrogen atom, or,
- C D : when taken together, a further single bond between the adjacent carbon atoms,
- $n$ : an integer which is 0 or 1,
- $m$ : an integer which is 0 or 1,
- $R_4$ : a methyl or ethyl group,
- $R_3$ : a methyl or ethyl group,
- $R_1$ : a hydrogen atom,
- $R_2$ : an ester group (e.g. $-COOR$ or $CH_2COOR$, where R is an alkyl group with from 1 to 6 carbon atoms), a 3,4-methylenedioxyphenyl group, or the group with the general formula (II) wherein Z is CH or a nitrogen atom, $p$ is 0 or 1, and X is $CH_3$, when $p$ is 1.

The compounds of the general formula (I) may be prepared, for example, by the following processes:

a. By etherformation (O-alkylation) between a compound of the general formula III and a compound of the general formula (IV),

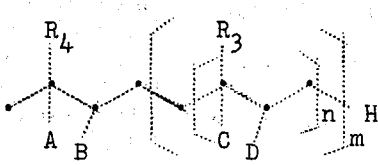 + 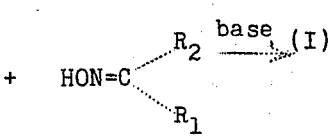

(III)    (IV)

wherein A, B, C, D, $n$, $m$, $R_4$, $R_3$, $R_2$, and $R_1$ have the same meaning as mentioned above and Hal. is chlorine, bromine or iodine.

b. By epoxydation of a compound of the general formula (III b) to form a compound of the general formula (III bb), followed by an etherformation according to process a to form a compound of the general formula (I b)

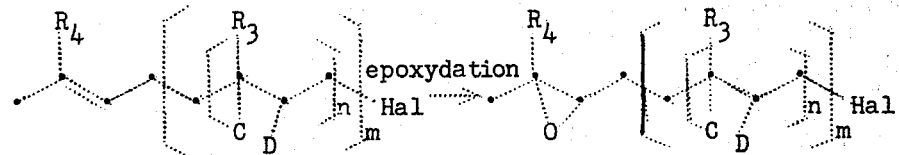

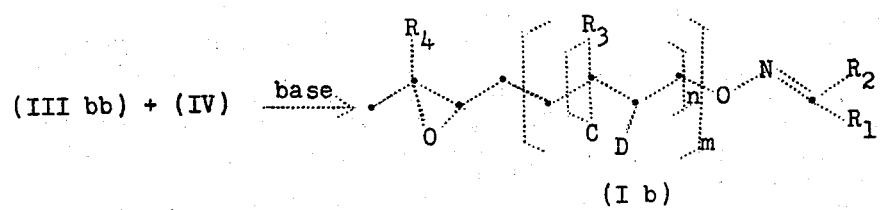

c. By alkoxylation of a compound of the general formula (III b) to form a compound of the general formula (III c), followed by an etherformation according to process a to form a compound of the general formula (I c)

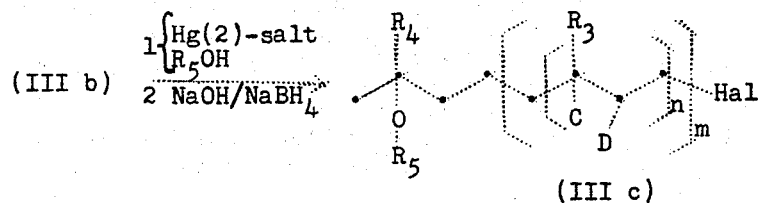

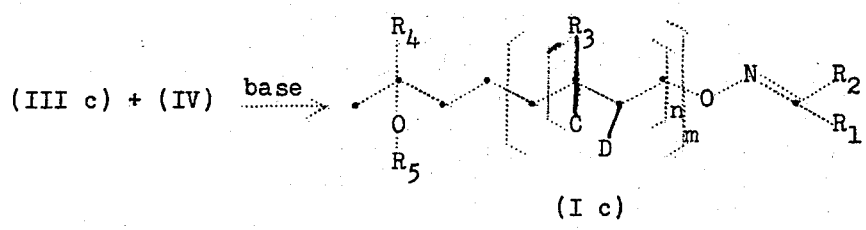

wherein $R_5$ is an alkyl group with from 1 to 6 carbon atoms.

Variations in these main processes due to variation in the starting material may for example be:

d. Process a, when A B taken together represent a single bond, C D taken together represent a single bond, n is one and m is one.
e. Process a, when A B taken together represent a single bond, C is hydrogen, D is hydrogen, n is one and m is one.
f. Process a, when A B taken together represent a single bond and $m$ is 0.
g. Process a, when A B taken together represent a single bond, $n$ is 0 and $m$ is 1.
h. Process b, when C D taken together represent a single bond, $n$ is 1 and $m$ is 1.
i. Process b, when C is hydrogen, D is hydrogen, $n$ is 1 and $m$ is 1.
j. Process b, when $m$ is 0.
k. Process b, when $n$ is 0 and $m$ is 1.
l. Process c, when C D taken together represent a single bond, $n$ is 1 and $m$ is 1.
m. Process c, when C is hydrogen, D is hydrogen, $n$ is 1 and $m$ is 1.
n. Process c, when $m$ is 0.
o. Process c, when $n$ is 0 and $m$ is 1.

The reaction according to process a between a compound of formula (III) and a compound of formula (IV) is preferably performed in the presence of a base and in an organic solvent, especially potassium hydroxide or sodium hydride in dimethylformamide.

The oximethers of formula (I) can, for example, be prepared according to this process from the chloride, bromide or iodide of the compound of formula (III) by reacting it with a 10% molar excess of the appropriate oxime of formula (IV) and powdered KOH in dimethylformamide. The reaction mixture is stirred for 3 to 20 hours at a temperature between 20° and 60°C, then diluted with water and extracted with ethylether. The organic extract is washed with a 10% KOH solution and finally washed with water. The extract is then dried over anhydrous $Na_2SO_4$, and the solvent is removed in vacuo. The resulting crude oximether is purified by column chromatography on silica gel, using a benzene/ethylacetate mixture in graduent elution.

The purity can be established to 99% by GLC and combined spectrometric methods.

The epoxydation process according to *b* is preferably performed with m-chloroperbenzoic acid as the epoxidation agent.

The compounds of formula (III *b*) can, for example, be epoxidized by reaction with m-chloroperbenzoic acid in methylenechloride at 0° to 5°C for 2 hours. A 10% molar excess of the peracid is used. After the epoxidation is completed, the reaction mixture is poured into an ice-cold 10% aqueous $NaHCO_3$ solution and is shaken thoroughly. The organic layer is then washed with water, dried over anhydrous $Na_2SO_4$, and the solvent is removed in vacuo.

The epoxy halogenide of formula (III *bb*) thus formed is reacted with an oxime of formula (IV) according to process *a* as described above, to form a compound of the general formula (I *b*).

In process *c*, the terminal alkoxylated compounds of the general formula (I *c*) can be prepared by the oxymercuration procedure of Brown, H. C. et al.: (J.A.C.S., 91, 5646, (1969)).

The alkenes of formula (III *b*) are, for example, treated with mercuric acetate in the appropriate alcohol i.e. the alcohol of formula $R_5OH$, resulting in the desired alkoxy group in the end product, and the resulting oxymercuric intermediate is reduced by adding aqueous 3 M NaOH and 0,5 $NaBH_4$ in 3 M NaOH. The mixture is allowed to stir for 2 hours, until the mercury has coagulated and settled. The reaction product is extracted with n-hexane, the extract washed with water, dried over anhydrous $Na_2SO_4$, and the solvent removed in vacuo. The resulting alkoxylated halogenides of formula (III *c*) are reacted with oximes of the general formula (IV) according to process *a* to form the terminal alkoxylated compounds of the general formula (I *c*).

The starting materials, oximes of the general formula (IV), may be made by standard methods from the appropriate carbonyl compounds and hydroxylamine hydrochloride.

The starting materials, halogenides of formula (III *b*), can, when *n* = *m* = 1, be either geranylbromide or -chloride, or citronellylbromide or -chloride. The halogenides of formula (III *b*) with shortened chainlength, e.g. *n* = *m* = 0 or *n* = 0 and *m* = 1, are made according to the reaction schemes below.

The Marc Julia synthesis.
(Bull. Soc. Chem. France, 1072, (1960))

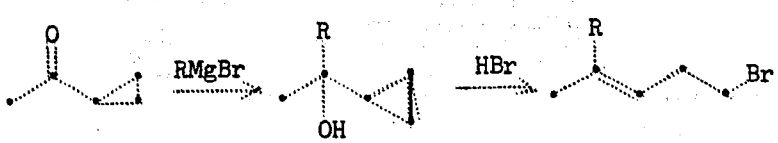

R = methyl or ethyl.
(Belg. patent No. 725 576)

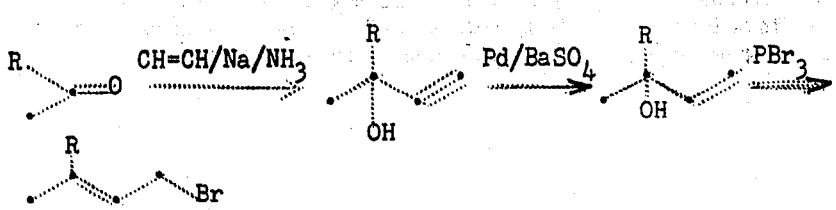

R = methyl or ethyl.
or, according to German Pat. No. 1,117,107

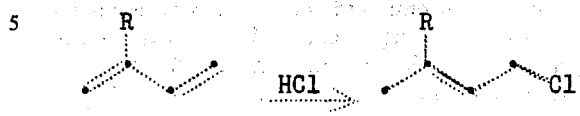

R = methyl or ethyl.

All chemical structures are confirmed by a combination of infrared and nuclear magnetic resonance (IR and NMR) data.

In accordance with the present invention, there is provided a method for the control of insects, which comprises contacting the insects, or their eggs or larvae, with a compound selected from those of formula (I) in an amount effective to inhibit the metamorphosis of said insect or to act as sterilizing or ovicidal agent.

Said compounds have found to act on species of different orders all over the class of insects, viz. Coleoptera (beetles, weevils), Lepidoptera (butterflies, moth), Hemiptera (bugs, plant lice, scales), Orthoptera (grass hoppers), Dictyoptera (roaches), and Diptera (flies, mosquitoes).

Accordingly, the invention also includes a composition containing a compound of the general formula (I) and a suitable carrier, which composition is suitable for the control of insect pests. To achieve a uniform distribution or application, it is advantageous to employ a composition comprising an inert carrier and, as the essential active ingredient, a compound of the general formula (I).

One method for the control of insects in accordance with the present invention is to apply the composition comprising an inert carrier and a compound of formula (I) to the locus of insect infestation, such as to the plant life on which insects live. These composition can be either solid or liquid.

Solid compositions for treating insects can be prepared by incorporating the active ingredient with an inert carrier such as finely divided talc, silica pyrophyllite, diatomite or clay or granular inert carriers, such as the vermiculites.

Liquid compositions can be prepared by mixing the active compound with inert carriers, such as acetone, xylene, peanut oil, cotton-seed oil, sesame oil and other vegetable oils and mineral oils conventionally employed as carriers in insecticidal formulation for application by spraying. Emulsions containing the active ingredient can also be used.

Other ingredients can be present in the composition of the present invention to aid in the effective application of the active ingredient, such as wetting agents, dispersing agents, insect attractants and the like.

The concentration of active ingredient of a compound of formula I in the composition can vary depending on a variety of factors, such as the specific insect involved, the degree of insect infestation, the locus of insect infestation, environment and weather conditions, and type of application device used.

Generally, the composition will contain less than 95% by weight of the active ingredient and more frequently less than 10% by weight.

The compounds of formula (I) are useful insect control agents by virtue of their ability to inhibit the metamorphosis of said insect. The expression "to inhibit the metamorphosis of said insect" as used herein, and in the appending claims, is used to describe the direct effect of the compounds of formula (I) as well as the indirect insecticidal effects of said compounds.

The compounds of formula (I) inhibit metamorphosis of various insect species at different stages, resulting in non-viable intermediates. Depending on the time of application, the compounds of formula (I) show ovicidal, larvicidal or pupicidal effect. When applied to the adult insect, the effect is indirect in the sense that the insect produces non-viable eggs.

The following examples are presented to illustrate the present invention.

EXAMPLE 1

Etherformation

Preparation of benzaldoxime-O-geranyl ether.

A mixture of 24.2 g. (0.20 mol) benzaldoxime and 13.0 g. powdered KOH (85%) in 200 ml. dimethylformamide is stirred for 30 min. 34.6 g. (0.2 mol) geranylchloride is added and the raection mixture is stirred over night at 50°–60°C. 200 ml. water is added to the reaction mixture, which is then extracted with ether. After separation the organic layer is washed with 10% KOH and with water until neutral. The extract is dried over anhydrous $Na_2SO_4$, and the solvent removed in vacuo. The yield was 38.2 g. of crude oximether, which was purified on silica gel as described below. $n_D^{24}$: 1.5202.

EXAMPLE 2

Epoxidation

Preparation of benzaldoxime-O-epoxygeranyl ether

To a stirred, chilled solution (0°C) of 3.4 g. geranylchloride in 100 ml. methylenechloride is cautiously added 4.5 g. (0.022 mol) 85% m-chloroperbenzoic acid in 30 ml. methylenechloride. The reaction mixture is stirred on an ice-bath for 2 hours, 10% aqueous $NaHCO_3$ solution is added and the mixture shaken thoroughly. The aqueous layer is extracted with methylenechloride and the combined extracts evaporated in vacuo. The residue is dissolved in ether, washed twice with 10% $NaHCO_3$ solution and finally twice with water. The etheral extract is dried over anhydrous $Na_2SO_4$ and evaporated in vacuo. 1.9 g. (0.01 mol) of crude 6,7-epoxygeranylchloride thus obtained is reacted with 1.2 g (0.01 mol) benzaldoxime in 10 ml. DMF in the presence of 0.7 g. KOH, according to the etherformation described above. For the actual oximether was found, $n_D^{24}$: 1.5255.

EXAMPLE 3

Alkoxylation

Preparation of benzaldoxime-0-(7-ethoxy-geranyl)-ether 3.4 g. geranylchloride (0.02 mol) is added to a vigorously stirred suspension of 6.4 g. mercurie acetate in 30 ml. of 99% ethanol at 0°C. One hour after the addition of the diene, the mercurial intermediate is reduced by adding 20 ml 0.5 M $NaBH_4$ in 3 M NaOH. The mixture is allowed to stir for 2 hours, until the mercury has coagulated and settled. Then the product is extracted with n-hexane, washed with water until neutral, dried over $Na_2SO_4$ and the solvent is removed in vacuo. 1.1 g. (0.005 mol) of crude 7-ethoxy-geranylchloride thus obtained is reacted with 0.6 g. (0.005 mol) benzaldoxime in 5 ml. DMF in the presence of 0.35 g. KOH, according to the etherformation described above. For the actual oximether was found, $n_D^{24}$: 1.5225.

EXAMPLE 4

Chromatography 10 g. crude benzaldoxime-O-geranylether is purified by column chromatography on silica gel (0.2–0.5 mm.). The column is filled with 250 g. silica gel and a benzene/ethylacetate mixture (4/1 by volume). The elution is started with a 4/1 mixture of benzene/ethylacetate (200 ml.), and then gradually increasing the concentration of ethylacetate during the elution: 3/1 (200 ml.), 7/3 (400 ml.), 3/2 (300 ml.) and finally 1/1 (200 ml.). The same procedure was applied to all other compounds.

EXAMPLE 5

Formulation

The active ingredient prepared according to Example 1 can be formulated in the following way:

| | |
|---|---|
| Active ingredient | 10,0 grammes |
| 70% Ca-dodecylphenylsulfonate | 5,0 grammes |
| Oleyl-poly(15)ethyleneoxideether | 5,0 grammes |
| Acetone | ad 100 millilitres (100 g/l a.i.) |

When poured into water, an emulsion is immediately formed, which shortly after is transformed into a true solution. Further dilution into any desired concentration can be performed.

The water based solution is ready for spraying.

In accordance with the given examples above, the following compounds has been prepared.

Table 1

| Comp. No. | Formula and name. | $n_D^{24}$ |
|---|---|---|
| 1 | Benzaldoxime-O-geranyl ether. | 1,5202 |
| 2 | Benzaldoxime-O-epoxygeranyl ether. | 1,5255 |
| 3 | Benzaldoxime-O-(7-methoxy-geranyl)-ether. | 1,5225 |
| 4 | Benzaldoxime-O-(3-ethyl-7-methyl-2,6-nonadiene-1-yl)-ether. | 1,5196 |
| 5 | Piperonaloxime-O-geranyl ether. | 1,5312 |
| 6 | p-Tolualdoxime-O-geranyl ether. | 1,5233 |
| 7 | 3-Pyridinealdoxime-O-geranyl ether. | 1,5350 |
| 8 | Benzaldoxime-O-citronellyl ether. | 1,5206 |
| 9 | Piperonaloxime-O-(3-methyl-2-pentene-1-yl)-ether. | 1,5596 |
| 10 | Benzaldoxime-O-(3-methyl-2-pentene-1-yl)-ether. | 1,5363 |

Table 1-continued

| Comp. No. | Formula and name. | $n_D^{24}$ |
|---|---|---|
| 11 | Piperonaloxime-O-(4-methyl-3-hexene-1-yl)-ether. | 1,5500 |
| 12 | Benzaldoxime-O-(4-methyl-3-hexene-1-yl)-ether. | 1,5303 |
| 13 | Glycollicaldoxime-O-geranyl ether. | 1,4905 |
| 14 | Glyoxylic acid ethylester aldoxime-O-geranyl ether. | 1,4682 |
| 15 | Glyoxylic acid ethylester aldoxime-O-(epoxygeranyl)-ether. | 1,4706 |
| 16 | Glyoxylic acid ethylester aldoxime-O-(7-ethoxy-geranyl)-ether | 1,4702 |
| 17 | Glyoxylic acid ethylester aldoxime-O-citronellyl ether | 1,4713 |
| 18 | Glyoxylic acid ethylester aldoxime-O-(7-methoxy-citronellyl)-ether | 1,4722 |
| 19 | Glyoxylic acid ethylester aldoxime-O-(3,7-dimethyl-octyl)-ether | 1,4453 |

Testing of juvenile hormone activity

The biological tests are exampified by tests on *Tenebrio molitor* L., *Galleria mellonella* L. and *Culex pipiens* L. *Tenebrio test*: The material in question is applied topically to the abdomen of 0.5 to 2 hours old pupae of the said specimen, as a solution in acetone. The pupae are held at 27°C and 70% RH, ecdysis occuring 5 to 7 days later. The degree of inhibition of adult characters is refered to an arbitrary scale, a morphologically perfect adult given the character 0%, a perfect second pupa 100%.

Galleria Test: The test is performed on recently laid eggs of *Galleria mellonella* by contact with impregnated filter paper. The data given in table 2, are the amount necessary for preventing eclosion of 50% of the eggs. The amount (IC-50 eclos.) is given in mg./65 cm$^2$.

Culex test: The compounds were tested on mature larvae of *Culex pipiens*. The concentration necessary to produce a loss of 50% of the test animals is given in table 2. (IC-50 eclos.) in ppm.

Table 2

| Comp. No. | Tenebrio test ID-50 morph. µg/pupa | Galleria test IC-50 eclos. mg/65 cm² | Culex test IC-50 eclos. ppm |
|---|---|---|---|
| 1 | 0,05 | >10 | <1,0 |
| 2 | >0,1 | — | — |
| 3 | 1,0 | 10 | 10 |
| 4 | 0,01 | — | — |
| 5 | >100 | 10 | 1,0 |
| 6 | 50 | 1,0 | 10 |
| 7 | 10 | — | — |
| 8 | >100 | 10 | <10 |
| 9 | 10 | 10 | 0,02 |
| 10 | >100 | 1,0 | 1,0 |
| 11 | >100 | 5 | 0,5 |
| 12 | >100 | 1,0 | <10 |
| 13 | 50 | — | 10 |
| 14 | 1 | — | 1,0 |
| 15 | 1 | — | 1,0 |
| 16 | 1 | 1 | 1,0 |
| 17 | — | 1,0 | — |
| 18 | — | 1,0 | — |

All compounds made and tested are mixtures of isomers.

What is claimed is:

1. A compound of the formula:

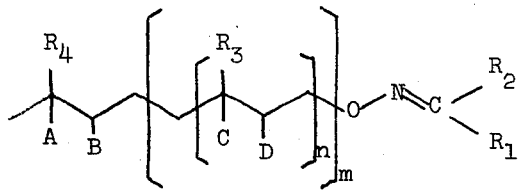

(I)

in which the symbols have the following meanings:

AB: are taken together and represent an oxygen atom;
C: a hydrogen atom, and
D: a hydrogen atom, or
CD: when taken together a further single bond between the adjacent carbon atoms,
$n$: an integer which is 0 or 1,
$m$: an integer which is 0 or 1,
$R_4$: a methyl or ethyl group,
$R_3$: a methyl or ethyl group,
$R_1$: a hydrogen atom, or an alkyl group having from 1 to 6 carbon atoms,
$R_2$: a 3,4-methylenedioxyphenyl group, or a group having the general formula II

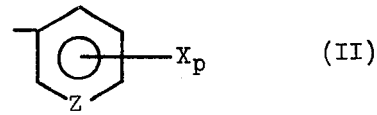

wherein Z is CH or a nitrogen atom, $p$ is an integer from 0 to 3, and X is a hydrogen atom or at least one substituent selected from the group consisting of $NO_2$, halogen, OH, $CF_3$, alkyl and alkoxy, which, when $p$ is 2 or 3, may be the same or different.

2. A compound according to claim 1 in which the symbols have the following meanings:
$R_2$: a 3,4-methylenedioxyphenyl group, or a group having the general formula II

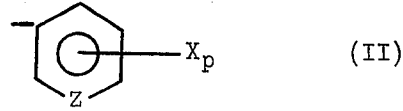

wherein Z is CH or a nitrogen atom, $p$ is 0 or 1, and X is an alkyl group having from 1 to 6 carbon atoms when $p$ is 1.

3. A compound as claimed in claim 2 wherein $R_1$ is a hydrogen atom.

4. A compound as claimed in claim 1, in which any of the groups alkyl or alkoxy represented by the symbol X contains from 1 to 6 carbon atoms.

5. A compound, as claimed in claim 1, in which the symbols have the following meanings:
$R_1$: a hydrogen atom, or an alkyl group having from 1 to 6 carbon atoms,
$R_2$: a 3,4-methylenedioxyphenyl group, or a group having the general formula II, wherein Z is CH or a nitrogen atom, $p$ is 0 or 1, and X is $CH_3$, when $p$ is 1.

6. A compound according to claim 1, which is benzaldoxime-O-epoxygeranyl ether.

* * * * *

UNITED STATES PATENT OFFICE
CERTIFICATE OF CORRECTION

PATENT NO. : 3,941,777
DATED : March 1, 1976
INVENTOR(S) : Hans Berg Madsen et al It is certified that error appears in the above–identified patent and that said Letters Patent are hereby corrected as shown below:

Applicants claim priority of British Application No. 60025/1972, filed December 29, 1972.

Signed and Sealed this twenty-ninth Day of June 1976

[SEAL]

Attest:

RUTH C. MASON
*Attesting Officer*

C. MARSHALL DANN
*Commissioner of Patents and Trademarks*